United States Patent [19]

Rebek

[11] Patent Number: 4,698,425

[45] Date of Patent: Oct. 6, 1987

[54] 1,3 DISUBSTITUTED AROMATIC CYCLOHEXANE IMIDES

[75] Inventor: Julius Rebek, Pittsburgh, Pa.

[73] Assignee: Year Laboratories, Inc., Los Angeles, Calif.

[21] Appl. No.: 634,053

[22] Filed: Jul. 24, 1984

[51] Int. Cl.$^4$ .......................................... C07D 401/14
[52] U.S. Cl. .................................. 544/235; 544/237; 544/238; 544/259; 544/260; 544/277; 544/322; 544/324; 544/333; 544/348; 544/353; 544/405; 546/107; 546/112; 546/183
[58] Field of Search ................ 546/187, 188, 107, 143, 546/162, 112, 183; 544/107, 239, 238, 277, 323, 260, 336, 235, 283, 291, 356, 259, 348, 322, 324, 333, 405, 353, 237

[56] References Cited

FOREIGN PATENT DOCUMENTS 0104346 4/1984 European Pat. Off.

OTHER PUBLICATIONS

Rebek-I, J. Amer., Chem. Sos., 106(4), pp. 1170–1171, (1984).
Rebek-II, "Abstracts of Papers", 187th A.C.S. National Meeting, (Apr. 1984), Paper ORGN-115.
Marshall, Luann—Dissentation Abstracts International, vol. 45/06-B, p. 1780.
R. D. Gandour, "On the Importance of Orientation in General Base Catalysis by Carboxylate", *Bioorganic Chemistry*, 10, 169–176, (1981).
D. S. Kemp and K. S. Petrakis, "Synthesis and Conformational Analysis of cis, cis, 1, 3, 5-Trimethylcyclohexane-1, 3, 5-Tricarboxylic Acid", *J .Org. Chem.*, 46, 5140–5143, (1981).
*Advanced Inorganic Chemistry*, 4th Ed., F.A. Cotton and G. Wilkinson, John Wiley, New York, 1980, pp. 283; 950; pp. 1016; 1314; 1315.
J. J. Wolf and R. E. Anderson, "Ion Exchange Purification of Feed Brine for Chlor-Alkali Electrolysis Cells". The Role of Duolite $^R$ Es-467. *Am. Inst. Chem. Eng.* Symposium Series, 78, 46–53, (1982).
W. Czuba and P. Kowalski, in the article entitled, "Direct Ring Benzylation of 2, 6-Diaminopyridine", in the *Polish Journal of Chemistry*, 55, at pp. 931 to 934, (1981).
Marshall, L. R., "The Design of Molecular Cavities: Allosteric Effects and Reaction Selectivity", Doctoral Thesis, University of Pittsburgh, 1984.
Anet, A. L. and Kopelevich, M., "Deuterium Isotope Effects on the Ring Inversion Equilibrium in Cyclohexane: The A Value of Deuterium and Its Origin", Journal of the American Chemical Society, vol. 108, pp. 1355–1356, 1986.
Winstein, S. and Holness, N. J., "Neighboring Carbon and Hydrogen. XIX, t-Butylcyclohexyl Derivatives. Quantitative Conformational Analysis", Journal of the American Chemical Society, vol. 77, pp. 5562–5578, 1985.

*Primary Examiner*—Robert J. Warden
*Assistant Examiner*—Robert Benson
*Attorney, Agent, or Firm*—Lyon & Lyon

[57] ABSTRACT

The compounds of the invention comprise the condensation product, as well as derivatives thereof, of two equivalents of a trimethyl cyclohexane-anhydride acid chloride derivative with one equivalent of an aromatic diamine. The scope of the invention includes the method of using the compounds of the invention as chelating agents for metals, metal ions or ions of metal complexes. In a preferred embodiment of the invention the binding moieties of the cyclohexane derivatives are rigidly held opposite each other, by restricting their rotation about the N-C aryl bonds, in order to more effectively bind the metals or the ions.

41 Claims, No Drawings

1,3 DISUBSTITUTED AROMATIC CYCLOHEXANE IMIDES

FIELD OF THE INVENTION

The invention relates to a class of newly discovered organic compounds and their use as chelating agents.

BACKGROUND OF THE INVENTION

Chelating agents are used extensively in, for example, the chemical industry, the mining industry, in medicine and in analytical research applications. For example, EDTA (Ethylenediamine tetraacetic acid) has been used to analyze for a number of transition metals. The structurally related imidodiacetic acid has been used to analyze for divalent metals such as calcium and cadmium.

Imidodiacetic acid is often used in industrial applications in a polymer bound form. The polymer bound forms include ion-exchange resins sold under the trademarks Amberlite IRC 718 TM, Dowex Al TM, and Chelex 100 TM, all of which are suitable for industrial applications and all of which are essentially imidodiacetic acid attached to an insoluble polymer support.

In using carboxylate ions for the binding of metals, binding is effected when the electron pairs of the oxygens are donated to the outer orbital of the metal ion moiety. It has been shown that the distal electron pairs of the oxygen atoms are more basic than the proximal electron pairs. The drawing below is illustrative of this concept.

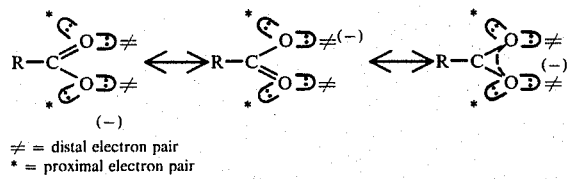

≠ = distal electron pair
* = proximal electron pair

See, R. D. Gandour, "On the Importance of Orientation in General Base Catalysis by Carboxylate." *Bioorganic Chemistry*, 10, 169–176 (1981).

In known chelating agents which employ carboxylate groups to bind metal ions—such as imido diacetate, dipicolinate and EDTA—generally only the proximal, less basic electron pairs are involved in binding the metals. Better metal ion binding would occur with a chelating agent which involves the more basic, distal, electron pairs of the oxygen atoms of a carboxylate group. Chelating agents also exist which employ as the active, binding functions, groups other than carboxylates—such groups include nitriles, thiol acids, amides, amidines, dithio acids, and hydroxamic acids. In these known chelating agents, as well as in imido diacetate, dipicolinate and EDTA, the active functions are generally not rigidly held in an optimal position for chelation, but rather will usually be freely rotatable such that they rotate through many positions where chelation cannot occur. Thus, the probability of metal binding is relatively low and the rate of metal binding is relatively slow and inefficient.

The recently discovered compound, cis-cis-1,3,5-trimethylcyclohexane-1,3,5-tricarboxylic acid, has been shown to prefer to exist, and to be more stable, in the conformation:

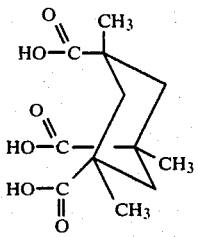

rather than the other possible conformation:

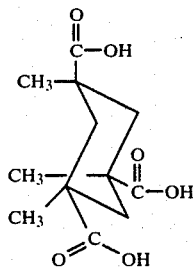

See, D. S. Kemp and K. S. Petrakis "Synthesis and Conformational Analysis of cis, cis, 1,3,5-Trimethylcyclohexane-1,3,5-Tricarboxylic Acid," *J. Org. Chem.*, 46, 5140–5143 (1981). Kemp and Petrakis have demonstrated that the methyl groups of this compound force a conformation in which any two of the carboxyl groups are rigidly maintained in the "C" shape illustrated above by the darkened lines in compound A. This shape is rigidly maintained in derivatives of compound A such as the acid chloride anhydride, which is one of the compounds from which the compounds of the invention are made, and has the structure;

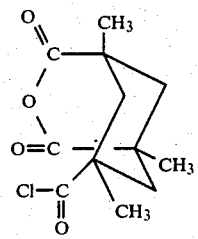

The shape illustrated by the darkened lines of compound A is also rigidly maintained in the imide bonded groups which are formed following reaction of compound C with a substituted or unsubstituted, fused or monocyclic, five or six membered diamine, wherein the amine groups have a 1,3 relationship. This reactions forms the compounds of the invention.

It is therefore an object of the invention to provide a chelating agent which can rigidly orient the active functions and preferably prevent rotation of the active functions through positions at which effective binding does not occur. It is a further object of the invention to provide a method of utilizing the compounds of the invention as effective chelating agents.

SUMMARY OF THE INVENTION

The compounds of the invention are condensation reaction products and their derivatives, of two equivalents of the above-illustrated acid chloride anhydride (compound C) with a fused or monocylic, substituted or unsubstituted, five or six membered aromatic diamine wherein the two NH₂ groups of the diamine have a 1,3 relationship. The reaction is carried out in a suitable solvent which will not react with the acid chloride anhydride, for example, pyridine, toluene, or benzene, and in the presence of a suitable reaction catalyst, for example, 4-dimethylaminopyridine. In the condensation reaction product the two acid chloride anhydride molecules form imide bonds with the two NH₂ groups and form two groups each having the structure:

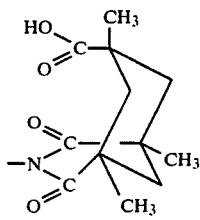

D these two groups also assume a 1,3 relationship in the compounds of the invention.

In other embodiments the carboxyl moieties of either or both of the two groups D can be substituted with any of the following moieties: nitriles; thiol acids (thiocarboxyls) amides; (amino carbonyls) amidines; (aminoiminomethyls) dithio acids (dithocarboxyls) and hydroxamic acids (hydroxyaminocarbonyls). Furthermore, the atom at the position of the aromatic ring which is between the 1,3 imide bonded ring atoms can, in different embodiments of the invention, be either a C or an N. Thus the compounds of the invention comprise a first group having the structure:

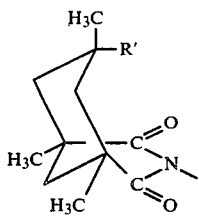

E and a second group having the structure:

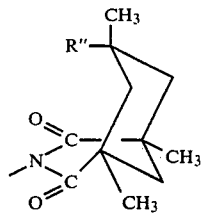

F imide bonded in a 1,3 relationship to a substituted or unsubstituted, fused or monocyclic, five or six membered aromatic compound, wherein a portion of the aromatic ring has the structure:

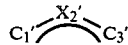

G

The groups E and F are imide bonded to $C_1'$ and $C_3'$ respectively, $X_2'$ is either N or CH, and R' and R" are either the same or different and are carboxyl, nitrile, thiol acid (dithiocarboxy), amide, amidine, dithio acid or hydroxamic acid moieties.

For example, the benzene derivative imide, one of the compounds of the invention, has the structure:

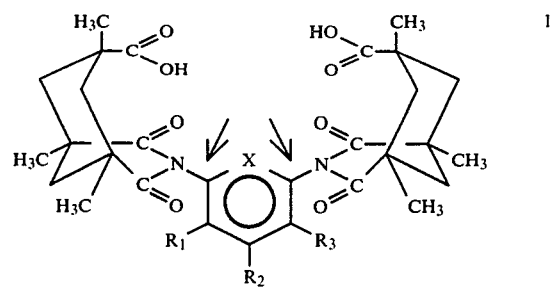

1 wherein X in compound 1 is $X_2'$ of structure G, and because compound 1 is benzene, X is CH. The term "A value" refers to the volume of space the electrons of a particular moiety occupy (Winstein, S.; Holness, N.J., *J. Am. Chem. Soc.* 1955, Vol. 77, pp. 5562–5578. "A value" defined as the conformational free energy difference in a monosubstituted cyclohexane). For reasons explained below, in a preferred embodiment, $R_1$ and $R_3$ have an A value larger than that of H. Thus $R_1$, $R_2$ and $R_3$ may be, for example, an H, an alkane, an alkyne, an alkene, a benzene, an aralkyl, a carbonyl, an ether, a thioether, a halide, a carbocycle or a heterocycle, or derivatives thereof.

The compounds of the invention are especially useful as chelating agents; in one preferred embodiment useful for binding some metal ions and their complexes, the active functions of the 1,3 di-imides of the invention are carboxyl groups attached to the cyclohexane moieties. In other embodiments of the invention, these carboxyl groups can be replaced with other active functions, such as COSH, CONHOH, CN, CONH₂, C(NH).NH₂, or CS₂H for preferential binding to certain metal ions and their complexes. It is believed that if the $X_2'$ atom of structure G is an N it will interact with the metal ion/metal complex and further enhance binding.

A feature of the compounds of the invention is that the rigidity of the aromatic heterocycles maintains the distance between the active functions and insures that the active functions will be properly oriented for chelating. If the active functions are carboxylates, then the distal basic electron pairs of one oxygen atom of each carboxylate will be available for binding; additionally both oxygens of both carboxylates will be available for binding. The schematic below is illustrative:

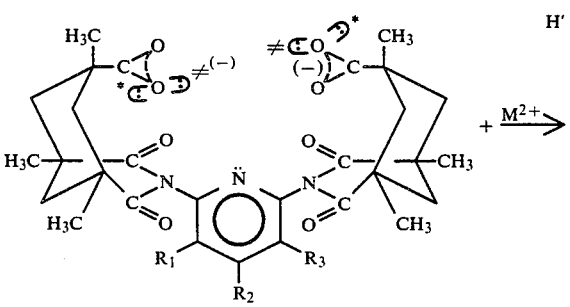

H'

-continued

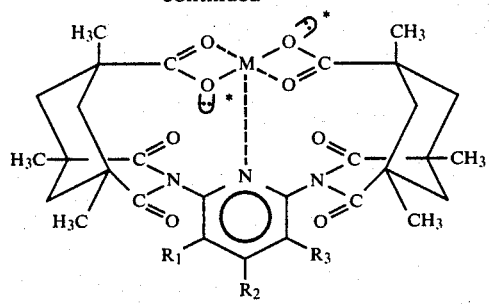

In the preferred compounds of the invention another feature is that the cyclohexane moieties are prevented from rotating about the N-C aryl bonds, shown by the arrows in compound 1. In compound 1, if the $R_1$ and $R_3$ groups are larger than H and thus have an A value larger than H, steric effects prevent rotation about the N-C aryl bonds—indicated by the arrows—and the novel vise-like shape shown is obtained. The shape and rigidity of compound 1 allow the carboxyl groups to converge on the metal ion/metal complex from opposite directions in the manner of a vise and all four oxygen atoms may participate in binding, as seen in schematic H'. Moreover, since rotation is prevented, if the active functions are groups other than carboxyls they will also be locked into an optimal binding orientation provided $R_1$ and $R_3$ have an A value larger than H.

The invention further comprises the method of utilizing the compounds of the invention as chelating agents, as more particularly described below.

DETAILED DESCRIPTION OF THE INVENTION

The compounds of the invention all include, as one portion of a fused or monocyclic aromatic ring, a structure 2' which may be schematically represented as:

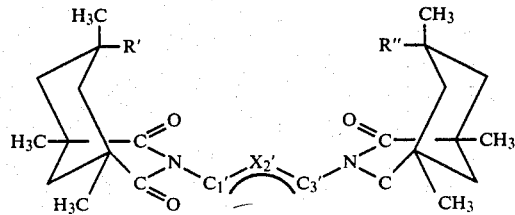

wherein the $C_1'$—$X_2'$—$C_3'$ structure is as described for structure structure G above, and each of R' and R" may be any of COOH, CN, C(NH) NH$_2$, CS$_2$H, COSH, CONHOH or CONH$_2$.

The subscripts 1,2 and 3 in structure 2' are used to indicate that $C_1'$, $X_2'$, and $C_3'$ all are positioned adjacent to one another and in sequence such that the imide bonded cyclohexane moieties have a 1,3 relationship in the aromatic ring. This adjacent, sequential positioning can best be depicted by way of example. The embodiments of the invention are defined by the composition of the R' and R" moieties, for example, R'=R"=COOH is one embodiment, and R'=R"=CN is another embodiment. The various species of the invention are those compounds which all have the same active functions, but are distinguished by the composition of the aromatic portions of the compound.

Using the 2' structure, the embodiments of the invention wherein the aromatic portion of the compound is benzene, are shown schematically as follows:

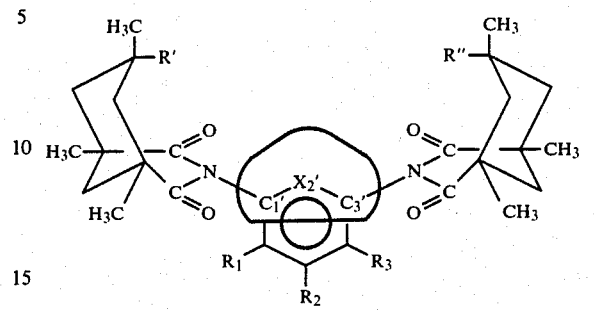

wherein $X_2'$ is CH, R' and R" are as defined for structure 2', and $R_1$, $R_2$ and $R_3$ are as defined for compound 1. The circled portion of compound 3 indicates the portion of the benzene ring which structure 2' occupies. As can be seen, the imide bonded cyclohexane groups have a 1,3 relationship.

Using the 2' structure, other embodiments of the invention wherein the aromatic portion of the compound is pyridine, are shown schematically as follows:

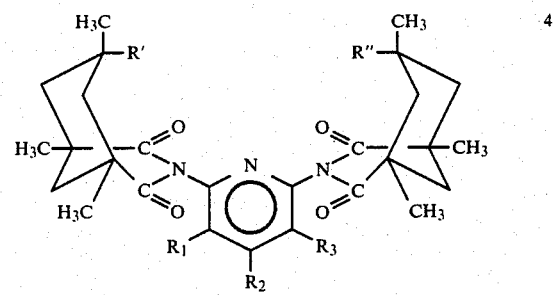

wherein $X_2'$ is N, R' and R" are as defined for structure 2', and $R_1$, $R_2$ and $R_3$ are as defined for compound 1. The imide bonded cyclohexane groups thus have a 1,3 relationship.

Using the 2' structure still other embodiments of the invention wherein the aromatic portion of the compound is a fused purinol diamine, are shown schematically as follows:

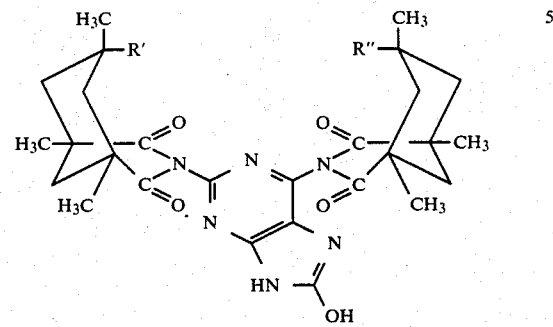

wherein $X_2'$ is N, R' and R" are as defined for structure 2', $R_1$ is not shown, and $R_2$ and $R_3$ are replaced by the fused imidazole ring which has an A value larger than H. Although not shown, an $R_1$ group could be bonded to the appropriate ring nitrogen atom of the pyrimidine portion of compound 5, for example of alkylation, resulting in this ring nitrogen atom carrying a positive charge. R groups could be similarly attached to other heterocycles in which either or both of the ring atoms adjacent the imide bonded ring atoms are nitrogens.

One species of the embodiments wherein the aromatic portion of the compound is 1,2,4-triazole, can be represented as:

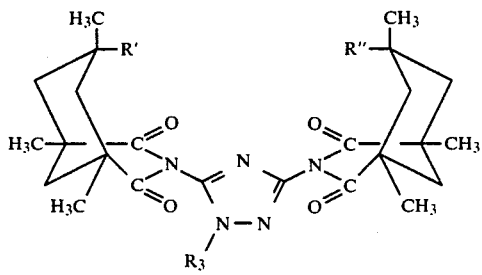

wherein R' and R" are as defined for compound 1 and $R_3$ has an A value larger than H. $R_1$ is not shown, however an R group could be bonded to the appropriate ring nitrogen, by a similar method to that described for the alkylation of compound 5.

Compound 7, which is one species of the embodiments in which the active functions are carboxyls, $X_2'$ of structure 2' is N, and an oxygen is covalently linked to the $X_2'$ nitrogen, has the structure:

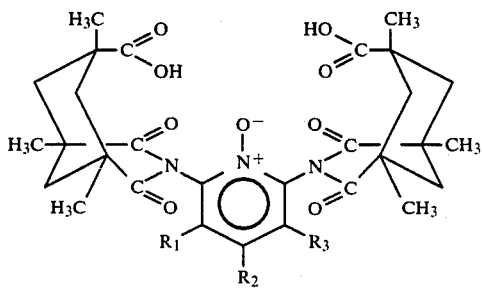

wherein the $R_1$ and $R_3$ groups have an A value larger than H.

Compounds 3 to 7 represent merely a few of the possible species of the various embodiments of the invention. In other species, structure 2' can be a portion of the ring of any fused or monocyclic, or substituted or unsubstituted, five or six membered, aromatic compound. Such aromatic compounds can include, substituted or unsubstituted benzene, pyridine, 1,2,4-triazole, purine, pyrimidine, pteridine, quinoline, isoquinoline, indole, imidazole, benzimidazole, naphthalene, pyridazine, pyrazine, thiophene, oxazole, thiazole, pyrazole, cinnoline, quinazoline, quinoxaline, phthalazine, acridine, and phenazine. The rigidity of the aromatic compounds maintains the distance between the cyclohexane derivatives and insures that the active functions (which are R' and R" in structure 2') are oriented for effective chelating.

As previously mentioned it is preferable to prevent rotation about the N-C aryl bonds in order to lock the active functions into an optimal binding position such that they converge from opposite directions on a metal ion/metal complex. In order to prevent such rotation $R_1$ and $R_3$ groups with an A value larger than H can be bonded to the appropriate ring atoms—i.e., those two ring atoms which are immediately adjacent but not between the imide bonded ring atoms ($C_1$ and $C_3$ in structure 2'). As will be appreciated by those skilled in the art, in some aromatic compounds (for example, thiazole and oxazole) one or both of the ring atoms which are immediately adjacent to the imide bonded ring atoms will not readily form exocyclic bonds. However, compounds with these difficult-to-bond-to sites are still within the scope of the invention.

In the fused ring aromatic species of the invention, if the fused ring is fused to both of these two immediately adjacent ring atoms, its relatively large A value will prevent rotation about the N-C aryl bonds. If only one fused ring is bonded to one of the immediately adjacent ring atoms, then rotation about the other N-C aryl bond can be prevented by bonding a group with an A value larger than H to the corresponding adjacent ring atom (provided it is capable of so bonding).

In addition to the previously described method wherein the compounds of the invention are formed from the acid chloride anhydride (compound C), it is also possible to form the compounds of the invention by heating the tricarboxylic acid (compound A) in the presence of an appropriate aromatic 1,3 diamine. Generally, the $R_1$, $R_2$ and $R_3$ groups will be attached to the aromatic 1,3 diamine prior to condensation with either of compounds A or C. Appropriate $R_1$, $R_2$, and $R_3$ groups can be attached to the majority of the aromatic 1,3 diamines by well-known methods. In the case of a pyridine diamine, a method of attaching a benzyl group thereto is described below in Example 4.

As will be appreciated by those skilled in the art, metals can be ionized to form metal ions, additionally, metals can form complexes with a wide variety of atoms and molecules and these complexes can also form ions, uranyl ion ($UO_2^{+2}$) being one example of such an ionized complex.

The invention also includes the method of use of any or all of the compounds of the invention as chelating agents. Prior to chelation of metals and their complexes, the embodiments of the invention wherein R' and R" are either the same or different and are any of a carboxyl, a hydroxamic acid, a dithio acid, or a thiol acid must be ionized. Ionization is performed by methods well known by those skilled in the art, as for example by dissolving these embodiments in a suitable polar solvent, such as water, the solvent also containing a suitable base, such as NaOH. The embodiments of the invention wherein R' and R" are amides, nitriles or amidines can be used for chelation in unionized form, however, it is preferable that chelation with these embodiments also be carried out in solution. Thus, in order to chelate, one adds the metals or metal complexes to a solution containing the compounds of the invention; the compounds of the invention will chelate effectively in either free or polymer bound form. Pursuant to the methods of this invention, one can remove hardness (meaning calcium and magnesium ions) from brine solutions. This selective removal is useful in the chlor-alkali industry as $Ca^{+2}$ must be removed from brine solutions to make the solutions acceptable for use in membrane-cell technology.

The compounds of the invention are useful chelating agents for a wide variety of metals and complexes. The embodiments of the invention wherein the R' and R" groups of structure 2' are carboxyls are particularly useful chelating agents for divalent ions such as calcium and magnesium. The carboxyl group embodiments of the compounds of the invention would also be useful for binding other metal ions in the same atomic group, (Column 2a of the Periodic Table), such as $Sr^{+2}$, $Ba^{+2}$ and $Ra^{+2}$. Lanthanides and Actinides which can exist in the +2 valence state, such as Sm, Eu, Yb, Md and No, could also be bound by these embodiments. Other metals and metal complexes known to prefer binding to oxygen containing ligands, for example $Hg^{+2}$, $Cd^{+2}$ and $UO_2^{+2}$, could also be bound by these carboxyl group embodiments. See, Cotton & Wilkinson, "Advanced Inorganic Chemistry" 4th Ed. p. 1016 and p. 283.

Compound 7 and other species of these embodiments of the invention which have an oxygen covalently bonded to the $X_2'$ heterocycle nitrogen, have an oxygen line cavity especially favorable for the binding of calcium and magnesium ions. It is anticipated that other metals in column 2a of the Periodic Table could be bound by these carboxyl group/oxygen embodiments of the invention.

The embodiments wherein R' is a carboxyl and R" is a nitrile are useful for binding monovalent silver.

The embodiments of the invention in which R' and R" of structure 2' are either the same or different and are any of CN, C(NH).$NH_2$, $CS_2H$, COSH and $CONH_2$, or the embodiments where R' is COOH and R" is any of the above-listed groups, are useful for binding ions which bind well to sulfur or nitrogen-containing ligands. Such ions include $Pt^{+2}$, $Pd^{+2}$, $Ni^{+2}$, $Co^{+2}$ and $Cu^{+2}$. Additionally, it is anticipated that other metals in the same columns of the Periodic Table (Column 2b and Group 8) such as Hg, Cd, Fe, Ru, Os, Rh and Ir, could be bound by these sulfur/nitrogen-ligand embodiments of the invention. Additionally, univalent metals, such as univalent copper, gold or silver could also be bound by these sulfur/nitrogen ligand embodiments of the invention.

The embodiments of the invention wherein R' and R" of structure 2' are both CONHOH, are useful for binding ions of iron and chromium. See, Cotton & Wilkinson "Advanced Inorganic Chemistry" 4th Ed. It is anticipated that other metals in Group 8 or Column 6b would also be bound by these hydroxamic acid-ligand embodiments of the invention.

Palladium can exist in a zero-valent state and in this state, will bind to nitrogen-containing ligands. Thus the embodiments wherein active functions are either the same or different and are any of a nitrile, an amide, or an amidine may bind zero-valent palladium.

The invention is further described in the following examples.

EXAMPLE 1

A compound 8 having the structure:

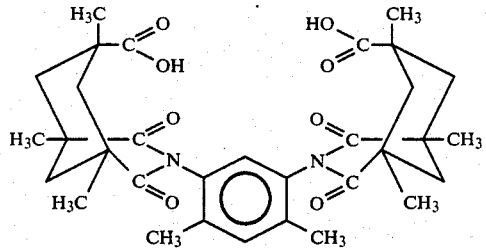

was used to extract calcium from an aqueous solution. Saturated $Ca(OH)_2$ in water (1 ml), was extracted with 2.0 ml of $CHCl_3$ containing 23 mg of compound 8. The organic and aqueous phases were separated and the organic phase was evaporated to give the calcium salt of compound 8 which had a melting point of greater than 300° C. The loss of $Ca^{+2}$ from the aqueous phase was determined by atomic absorption spectroscopy.

EXAMPLE 2

For commercial and industrial applications chelating agents are generally used in a polymer-bound form. The compounds of the invention, including compounds 3 to 8, can be bound to a suitable insoluble polymer support, such as Merrifield's resin. A typical extraction procedure using one of the compounds of the invention bound to Merrifield's resin, would be to pass an aqueous solution of metal ions through a column containing the compound bound to Merrifield's resin, and then to wash the column, for example with aqueous HCl, to release the metal ions. As will be apparent to those skilled in the art, this extraction procedure would be suitable for extraction of a wide variety of metals and metal complexes from solution and could also be used with the compounds of the invention bound to suitable insoluble polymer supports other than Merrifield's resin.

EXAMPLE 3

Compound 8, was prepared by dissolving 291 mg of 1,3-diamino-4,6-dimethyl-benzene and 1.1 g of compound C, described above, in 10 ml of dry pyridine containing 20 mg of 4-dimethylaminopyridine (which acts as a reaction catalyst), and heating the solution at 90° C. for 16 hours under a nitrogen atmosphere. The solvent was evaporated at reduced pressure and the remaining solid was dissolved in $CHCl_3$ and washed three times with 3N HCl. After drying with $MgSO_4$ the $CHCl_3$ was evaporated to give 1.24 g of compound 8 having a melting point of greater than 350° C. The compound showed IR absorption, using chloroform as the solvent, at 1690, 1705 and 1730 1/cm. A similar procedure to that used to prepare compound 8, could be used to prepare any of the species of compound 1 by selecting as one of the compounds of the reaction, a 1,3 disubstituted benzene diamine with the appropriate $R_1$, $R_2$ and $R_3$ groups. Additionally, a similar procedure was used to prepare a compound 8(a) having the structure of compound 1, wherein $R_2=CO_2CH_3$ and $R_1=R_3=H$.

EXAMPLE 4

The compounds of the invention could be attached to a suitable insoluble polymer support by any of several methods known to those skilled in the art. One such method would be to alkylate 2,6 diamino pyridine with chloromethylated, crosslinked polystyrene (Merrifield's resin). This can be accomplished by heating a mixture of 2,6 diamino pyridine and Merrifield's resin to about 250° C. for one to five hours. Following bonding to Merrifield's resin, this compound could be condensed with the acid chloride anhydride (compound C) by reaction in a suitable solvent, for example, toluene, pyridine or benzene, and in the presence of a suitable reaction catalyst, for example 4-dimethylamino pyridine. The resulting compound 9 would have the structure:

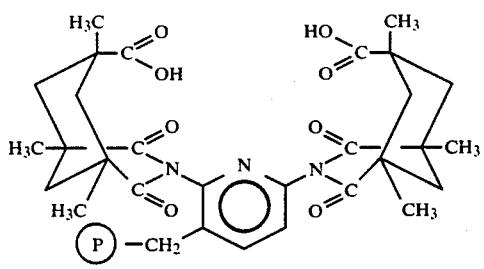

wherein P represents Merrifield's resin.

EXAMPLE 5

Another method of bonding the compounds of the invention to a suitable insoluble polymer support would be to select a compound of the invention having an amine group bonded at one position of the aromatic ring, and then to bond this compound to chlorosulfonated, macroreticular, cross linked polystyrene thus forming a sulfonamide bonded compound 10, having the structure:

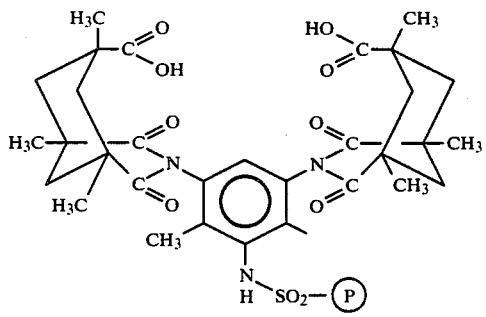

wherein P represents the polymer support.

As will be appreciated by those skilled in the art, a number of variations of this method could be used. For example, a chlorosulfonated compound of the invention in combination with an aminomethylated polymer could be reacted so as to link the compound to the support. Additionally, a similar procedure, known to those skilled in the art as the Hofmann-Martius reaction, could be used to link benzyl, methyl benzyl, methoxybenzyl, or chlorobenzyl to 2,6-diaminopyridines, thereby yielding a 3,5-disubstituted 2,6-diaminopyridine. These products will have $R_1$ and $R_3$ groups with an A value such that rotation about the N—C aryl bonds will be prevented when these products are used to form the compounds of the invention.

EXAMPLE 6

Direct alkylation of suitable species of any of the embodiments of the present invention would also be possible as a means of linking these compounds to Merrifield's resin or other water insoluble polymer supports. A compound 11, one species of the embodiments of the invention wherein $R'=R''=COOH$, and the aromatic portion of the compound is pyrimidine, having the structure;

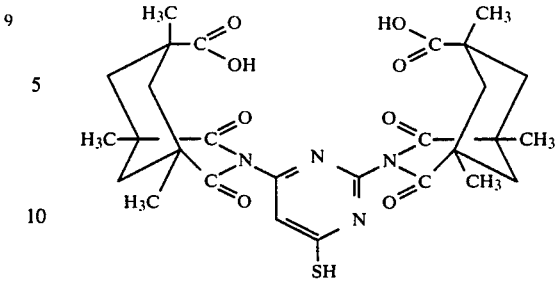

could be attached to Merrifield's resin through S-alkylation to produce a compound 12, having the structure;

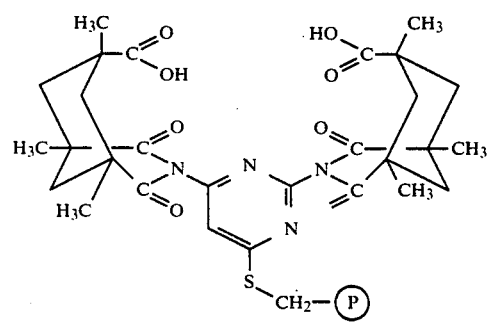

wherein P represents Merrifield's resin. Compound 12 would also be useful for recovery of divalent metals from dilute solutions. Similarly, other embodiments of the species invention which have a thio group attached to an aromatic ring could be directly alkylated to link these compound to a water insoluble polymer support.

EXAMPLE 7

A compound 13, one species of the embodiments wherein $R'=R''=COOH$, the aromatic portion of the compound is pyridine, and $R_1=R_3=CH_2\text{-}C_6H_5$, $R_2=H$, has the structure:

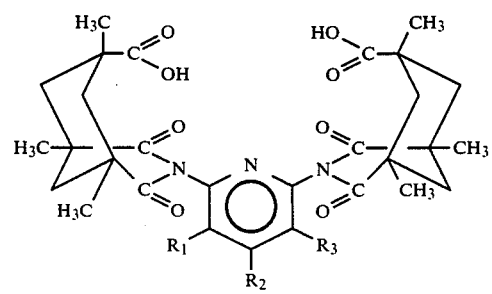

Compound 13 was prepared from a solution of 2,6-diamino-3,5-dibenzyl pyridine, 150 mg of poly-4-vinylpyridine, 5 mg of 4-dimethylaminopyridine, and 195 mg of compound C in 3 ml of toluene. The solution was heated at reflux for 140 hours under a nitrogen atmosphere. After cooling to room temperature, the polymer was removed by filtration and the filtrate was evaporated. Chromatography on a silica gel column using ETOAc/Hexane (1:1) as the eluent yielded 145 mg of compound 13, appearing as a pale yellow solid with a melting point of greater than 340° C. Compound 13 showed IR absorption, using chloroform as the solvent, at 1690, 1715, 1740 and 2900 1/cm. A similar procedure was used to prepare compounds 14 and 15, also having pyridine as the aromatic portion of the compound, with $R'=R''=COOH$, wherein the various $R_1$, $R_2$ and $R_3$ groups listed below indicate the different compound compositions:

(Compound 14) $R_1=R_2=R_3=H$;

(Compound 15) $R_1=R_3=CH_2C_6H_4CH_3$, $R_2=H$.

A similar procedure could be used to make other embodiments having pyridine as the aromatic portion of the compound, and having other $R_1$, $R_2$, and $R_3$ groups attached thereto.

EXAMPLE 8

Compound C (94.6 mg, 0.367 mmol), 2,4-diamino-6-hydroxypyrimidine (21.5 mg. 0.170 mmol) and a small amount of poly(4-vinyl)pyridine were heated at 90° C. in 3 ml toluene under a $CaCl_2$ drying tube. After cooling, the mixture was filtered to remove the polymeric base. The residue, after evaporation, was taken up in $CHCl_3$ and washed twice with 1N HCl and then once with brine. Evaporation yielded 62.1 mg of compound 16, which appeared as a tan solid with a melting point of about 225°–250° C.

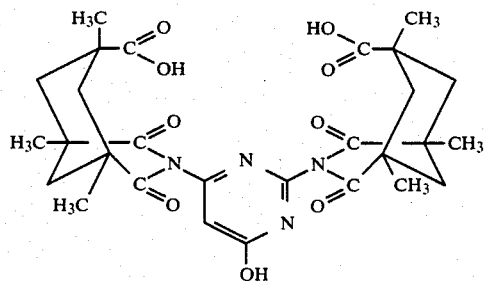

A similar method could be used to prepare other species wherein pyrimidine is the aromatic portion of the compound.

EXAMPLE 9

A compound 17, with the benzene as the aromatic portion of the compound, having the structure:

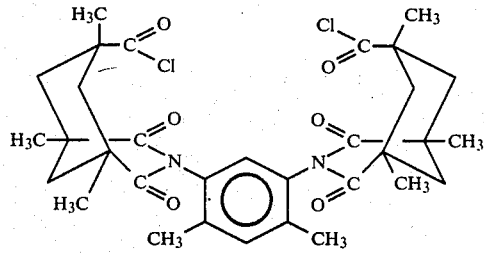

was prepared by heating at 60° C. under a $CaCl_2$ drying tube for 12 hours, 107 mg of compound 8 in 3 ml of $SOCl_2$. The solvent was thereafter evaporated at reduced pressure to produce a solid which was chromatographed on silica gel with a 1:1 mixture of EtOAc/Hexane to give 111 mg of compound 17.

Compound 17 had a melting point of between 297° C. and 303° C. and showed IR absorption, in chloroform, at 1690, 1730, 1760, 1785 and 1805 1/cm.

Acid chloride embodiments of other species of the invention which have carboxylic acids as the active functions, could be prepared by a similar method to that outlined for the preparation of compound 17. Suitable reactants, reaction conditions, and solvents will be readily apparent to those skilled in the art.

EXAMPLE 10

One species of the embodiments wherein $R'=R''=CONH_2$, the aromatic portion of the compound is benzene, $R_1=R_3=CH_3$ and $R_2=H$ having the formula;

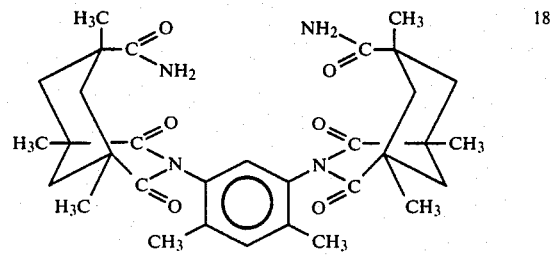

was prepared by bubbling ammonia gas for 10 minutes into a $CaCl_2$ drying tube containing a solution of 60 mg of compound 17 and 5 ml tetrahydrofuran. The solvent was removed in vacuo and the residue was taken up in $CHCl_3$, washed with $H_2O$, dried over $MgSO_4$, and concentrated to yield compound 18.

Compound 18 had a melting point of 340°–342° C. and showed IR absorption in chloroform at 1670, 1690, 1730 and 3100–3250 1/cm. The mass spectrum M/e was at 578, 554, 357 and 236. Amide embodiments of other species of the compounds of the invention could be prepared by a method similar to the method of preparing compound 18.

Compound 18, and other amide embodiments of the invention, can be dehydrated, by a process well known to those skilled in the art, to yield a species of a nitrile embodiment of the invention, with the aromatic portion being benzene, and wherein $R_2=H$, $R_1=R_3=CH_3$. Nitrile embodiments of other species, wherein the aromatic portion is other than a benzene, can be prepared by a similar process. Suitable reactants and reaction conditions will be readily apparent to those skilled in the art.

EXAMPLE 11

$H_2S$ gas, after having been first bubbled through $H_2O$, was bubbled into 65 mg of compound 17, dissolved in about 1 ml of pyridine. Following bubbling for 20 minutes, the reaction mixture was evaporated. Chromatography on silica gel with ethyl acetate as the eluent yielded 41 mg of compound 19 appearing as a pale tan solid. IR absorption in $CDCl_3$ was at 1600–1700, 1730 and 1750 1/cm.

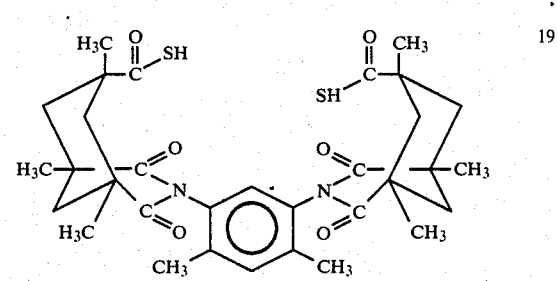

15

Thiol acid embodiments of other species, wherein the aromatic portion of the compound is other than benzene, can be prepared by a method similar to that used to prepare compound 19.

EXAMPLE 12

A solution of excess $H_2NOH\cdot HCl$ in pyridine was added dropwise to 65 mg (0.105 mmole) of compound 17 dissolved in 0.5 ml pyridine. The yellow-orange solution was stoppered and left stirring overnight. After evaporation of the volatiles, $CHCl_3$ was added and the organic phase washed twice with 10 ml of 1N HCl. Evaporation of the organic solution yielded the compound 20 which was recrystallized from ethylacetate/hexane. Mass spectrum showed peaks at 610, 582, 554 and 490.

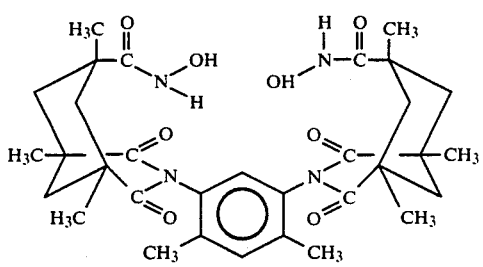

Hydroxamic acid embodiments of other species could be similarly prepared.

EXAMPLE 13

Compound 8, or other species of carboxyl embodiments of the invention, can be used to prepare a compound with a blocked R' group, one such species being compound 21 having the structure:

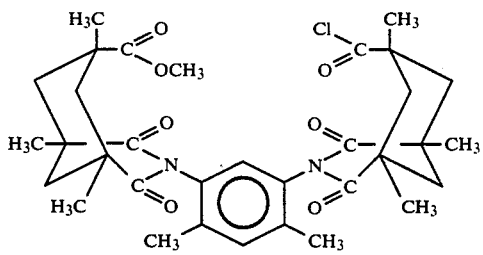

Compound 21 can be prepared by treating compound 8 with 1 equivalent of $Me_3O^+BF_4^-$ in the presence of $EtN(i-Pr)_2$ in methylene chloride to yield the methyl monoester. Once the one methyl monoester shown in compound 21 is formed, the space in the molecule is insufficient to allow the other carboxylic acid group to also form a methyl monoester at a rapid rate. The methyl monoester compound can be reacted with $SOCl_2$ to yield compound 21. Reacting compound 21 with $NH_3$ can produce the ester amide (not shown) which in turn can be used to produce the ester-nitrile (not shown) by well-known methods. The ester-nitrile so produced can be used to produce a species of the embodiments wherein R'=COOH and R"=CN, by alkaline hydrolysis. Other species of the embodiments of the invention having different aromatic portions than compound 21, and with these same active functions, could be similarly prepared.

Additionally, a similar procedure, wherein one COOH group is blocked with a methyl monoester, could be used to prepare embodiments where one active function is COOH and the other is any of $C(NH)NH_2$, $CS_2H$, COSH, CONHOH, or $CONH_2$. Similarly, any embodiment of the invention wherein R' and R" are different can be prepared by well known methods, following blocking of either R' or R" with a methyl monoester as described above, and then performing the appropriate chemical conversions.

EXAMPLE 14

One species of compound 7 wherein $R_1=R_3=CH_2-C_6H_5$, $R_2=H$, can be produced by heating under reflux compound 13 in $CH_2Cl_2$ containing an excess of 85% m-Cl-perbenzoic acid. After cooling, the solution could then be successively washed with $CaCl_2$ in TRIS buffer, with 1N HCl, and thereafter dried over $Na_2SO_4$. The solvent would thereafter be evaporated to yield compound 7. Various species of the embodiments of the invention with the same active functions as compounds 7 and with an oxygen ion covalently bonded to the ring nitrogen, could be similarly prepared.

It should be understood that other compounds can be prepared wherein the cyclohexane derivatives could be bound to molecules other than aromatic compounds. Accordingly, the terms and expressions used herein are terms of description and not of limitation, and the invention is thus limited only by the scope of the claims which follow.

What is claimed is:

1. A compound comprising a first group having the structure,

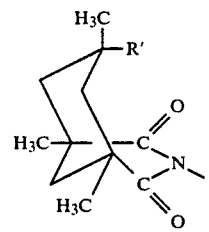

and a second group having the structure,

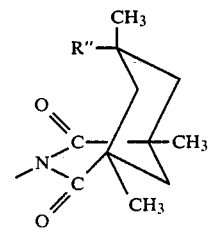

bonded by the imide nitrogens in a 1,3 relationship to a fused or monocyclic, substituted or unsubstituted, five or six membered aromatic compound, wherein a portion of the ring structure is,

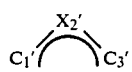

and wherein said imide nitrogens are bonded to $C_1'$ and $C_3'$ respectively, $X_2'$ is either N or CH and R' and R" are either the same or different and each is a moiety selected from the group consisting of carboxyl, nitrile, hydroxyaminocarbonyl, thiocarboxy, dithiocarboxy, aminoiminomethyl and amino carbonyl.

2. The compounds of claim 1 wherein $X_2'$ is N and R' and R" are both carboxyls, further including an oxygen atom covalently bonded to said nitrogen atom which is at said $X_2'$ position.

3. A compound comprising the condensation reaction product of two equivalents of a compound having the structure,

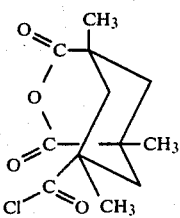

with one equivalent of a fused or monocyclic, substituted or unsubstituted, five or six membered aromatic diamine, wherein the two $NH_2$ groups have a 1,3 relationship and the one ring atom which is between the ring atoms to which the $NH_2$ groups are 1,3 bonded is either C or N, and the compound formed by said condensation reaction has two groups each having the structure,

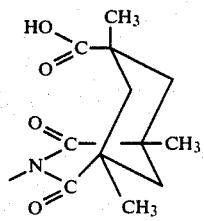

imide bonded in a 1,3 relationship to a fused or monocyclic, substituted or unsubstituted, five or six membered aromatic compound.

4. The compound of claim 1 wherein at least one of the two ring atoms which are immediately adjacent but not between $C_1'$ and $C_3'$ is either C or N having a group with an A value larger than H bonded thereto.

5. The compound of claim 2 wherein at least one of the two ring atoms which are immediately adjacent but not between $C_1'$ and $C_3'$ is either C or N having a group with an A value larger than H bonded thereto.

6. The compound of claim 3 wherein at least one of the two ring atoms which are immediately adjacent but not between the two ring atoms to which the two $NH_2$ groups are 1,3 bonded is either C or N having a group with an A value larger than H bonded thereto.

7. The compound of claim 1 wherein said aromatic compound is selected from the group consisting of, substituted or unsubstituted, benzene, pyridine, 1,2,4-triazole, purine, pyrimidine, pteridine, quinoline, isoquinoline, indole, imidazole, benzimidazole, naphthalene, pyridazine, pyrazine, thiophene, oxazole, thiazole, pyrazole, cinnoline, quinazoline, quinoxaline, phthalazine, acridine and phenazine.

8. The compound of claim 2 wherein said aromatic compound is selected from the group consisting of, substituted or unsubstituted, pyridine, purine, pyrimidine, 1,2,4-triazole, isoquinoline, imidazole, pyrazine, oxazole, thiazole, quinazoline, and pteridine.

9. The compounds of claim 3 wherein said aromatic diamine is substituted or unsubstituted, benzene, pyridine, 1,2,4-triazole, purine, pyrimidine, pteridine, quinoline, isoquinoline, indole, imidazole, benzimidazole, naphthalene, pyridazine, pyrazine, thiophene, oxazole, thiazole, pyrazole, cinnoline, quinazoline, quinoxaline, phthalazine, acridine or phenazine wherein the two $NH_2$ groups have a 1, 3 relationship.

10. A compound having the structure,

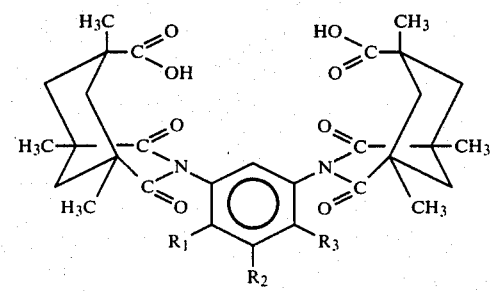

wherein $R_1$, $R_2$ and $R_3$ are either H or a group with an A value larger than H.

11. The compound of claim 10 wherein $R_2$ is H and $R_1$ and $R_3$ are both $CH_3$.

12. The compound of claim 10 wherein $R_1$ and $R_3$ are both H, and $R_2$ is $CO_2CH_3$.

13. A compound having the structure,

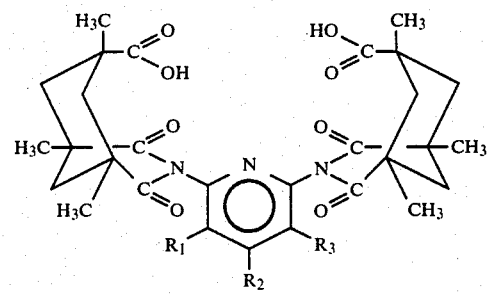

wherein $R_1$, $R_2$ and $R_3$ are either H or a group with an A value larger than H.

14. The compound of claim 13 wherein $R_1$, $R_2$ and $R_3$ are selected from one of the following combinations:

$R_1=R_2=R_3=H$;

$R_1=R_3=CH_2C_6H_5$, $R_2=H$;

$R_1=R_3=CH_2C_6H_4CH_3$, $R_2=H$.

15. The compound of claim 13 wherein an oxygen atom is covalently bonded to the pyridine ring nitrogen.

16. A compound having the structure:

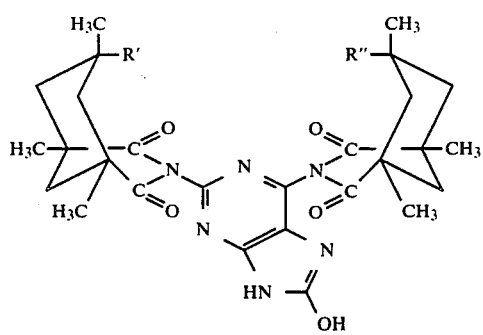

wherein R' and R" are either the same or different and are selected from the group consisting of carboxyl, nitrile, hydroxyaminocarbonyl, thiocarboxy, dithiocarboxy, aminoiminomethyl and amino carbonyl moieties.

17. A compound having the structure,

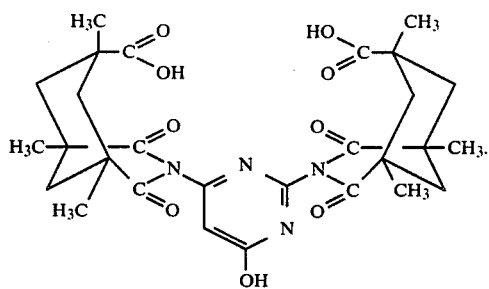

18. The compound of claim 17 wherein an oxygen atom is covalently bonded to the ring nitrogen which is located between the imide bonds.

19. A compound having the structure,

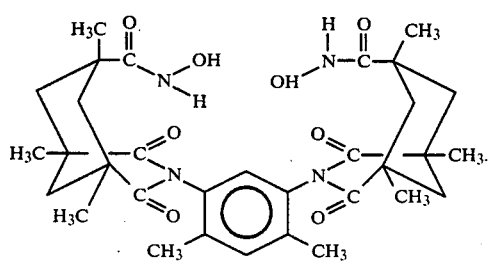

20. A compound having the structure,

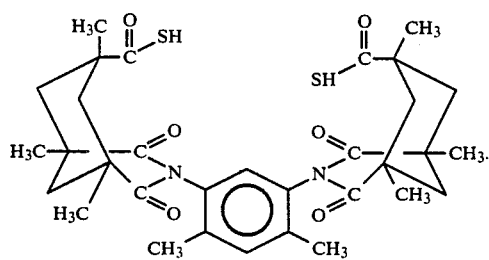

21. A compound having the structure,

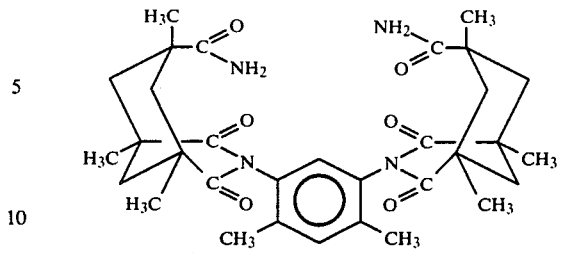

22. The compound of claim 1 wherein R' is COOH and R" is CN.

23. The compound of claim 22 wherein at least one of the two aromatic ring atoms which are immediately adjacent but not between $C_1'$ and $C_3'$ are either C or N having a group with an A value larger than H bonded thereto.

24. The compounds of claims 4, 5, 6, 10, 13, or 23 wherein said group with an A value larger than H is a stable group comprising at least one atom selected from the group consisting of carbon, nitrogen, oxygen, silicon, phosphorous, sulphur, fluorine, chlorine, bromine, and iodine which atom is directly bonded to the C or N which is adjacent, but not between the imide bonded atoms.

25. The compound of claims 1, 2, 3, 4, 5, 6, 7, 8 or 9 wherein said compound is bonded to an insoluble polymer support suitable for use in chelating metals, metal complexes and metal ions.

26. The compound of claim 25 wherein said compound is bonded to said insoluble polymer support by a thioalkyl bond.

27. The compound of claim 25 wherein said compound is bonded to said insoluble polymer support by a sulfonamide bond.

28. The compound of claim 25 wherein said suitable insoluble support is a chloromethylated, cross-linked polystyrene.

29. The compounds of claim 14 wherein, when $R_1=R_3=CH_2C_6H_5$ and $R_2=H$, said compound is bonded to an insoluble polymer support suitable for use in chelating metals, metal complexes or metal ions.

30. The compound of claim 29 wherein said polymer support is a crosslinked polystyrene.

31. Compounds having the structure

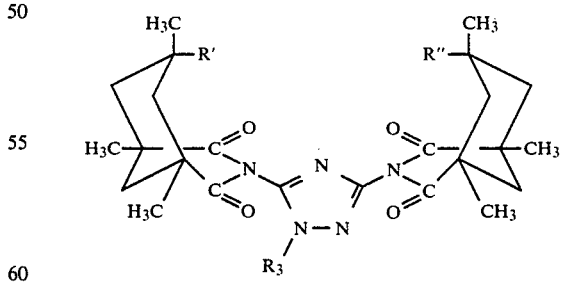

wherein R' and R" are selected from the group consisting of COOH, CN, C(NH)NH$_2$, CS$_2$H, COSH, CONHOH and CONH$_2$ and R$_3$ is H or an insoluble polymer support suitable for use in chelating metals, metal complexes or metal ions.

32. The compounds of claim 31 wherein R'=R"=COOH and R$_3$=H.

33. The compounds of claim 31 wherein R'=R''=COOH and $R_3$ is a crosslinked polystyrene.

34. The compounds of claims 10, 11, 12, 13, 15, 16, 17, 18, 19, 20, 21, 22, or 23 wherein said compound is bonded to an insoluble polymer support suitable for use in chelating metals, metal complexes and metal ions.

35. The compounds of claim 34 wherein said compound is bonded to said insoluble polymer support by a thioalkyl bond.

36. The compounds of claim 34 wherein said compound is bonded to said insoluble polymer support by a sulfonamide bond.

37. The compounds of claim 34 wherein said suitable insoluble support is chloromethylated, cross-linked polystyrene.

38. The compounds of claim 24 wherein said compound is bonded to an insoluble polymer support suitable for use in chelating metals, metal complexes and metal ions.

39. The compounds of claim 38 wherein said compound is bonded to said insoluble polymer support by a thioalkyl bond.

40. The compounds of claim 38 wherein said compound is bonded to said insoluble polymer support by a sulfonamide bond.

41. The compounds of claim 38 wherein said suitable insoluble support is chloromethylated cross-linked polystyrene.

* * * * *